US00PP26931P2

(12) United States Plant Patent
Wicki-Freidl

(10) Patent No.: US PP26,931 P2
(45) Date of Patent: Jul. 12, 2016

(54) ***LOBULARIA* PLANT NAMED 'INLOBU1007'**

(50) Latin Name: *(Lobularia canariensis×Lobularia maritima)×Lobularia maritima*
Varietal Denomination: Inlobu1007

(71) Applicant: Barbara Freidl, Nesslau (CH)

(72) Inventor: Peter Wicki-Freidl

(73) Assignee: InnovaPlant Zierpflanzen GmbH + Co. KG, Gensingen (DE)

( * ) Notice: Subject to any disclaimer, the term of this patent is extended or adjusted under 35 U.S.C. 154(b) by 44 days.

(21) Appl. No.: 14/121,726

(22) Filed: Oct. 11, 2014

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Anne Grunberg
(74) *Attorney, Agent, or Firm* — C. A. Whealy

(57) ABSTRACT

A new and distinct cultivar of *Lobularia* plant named 'Inlobu1007', characterized by its compact, outwardly spreading, mounding and semi-trailing plant habit; freely branching habit; freely and continuous flowering habit; relatively long flowering period; small violet-colored flowers; and good garden performance.

1 Drawing Sheet

Botanical designation: (*Lobularia canariensis*×*Lobularia maritima*)×*Lobularia maritima.*

Cultivar denomination: 'INLOBU1007'.

BACKGROUND OF THE INVENTION

The present invention relates to a new and distinct cultivar of *Lobularia* plant, botanically known as (*Lobularia canariensis*×*Lobularia maritima*)×*Lobularia maritima* and hereinafter referred to by the name 'Inlobu1007'.

The new *Lobularia* plant is a product of a planned breeding program conducted by the Inventor in La Palma, Canary Islands, Spain. The objective of the breeding program was to develop new compact and semi-trailing *Lobularia* plants with numerous small flowers.

The new *Lobularia* plant originated from a cross-pollination conducted by the Inventor in March, 2009 in La Palma, Canary Islands, Spain of a *Lobularia canariensis*×*Lobularia maritima* 'Inlbusnopr', disclosed in U.S. Plant Pat. No. 21,594, as the female, or seed, parent, with an unnamed selection of *Lobularia maritima*, not patented, as the male, or pollen, parent. The new *Lobularia* plant was discovered and selected by the Inventor as a single flowering plant within the progeny of the stated cross-pollination in a controlled greenhouse environment in La Palma, Canary Islands, Spain in May, 2010. Asexual reproduction of the new *Lobularia* plant by vegetative cuttings in a controlled greenhouse environment in Gensingen, Germany since June, 2010 has shown that the unique features of this new *Lobularia* plant are stable and reproduced true to type in successive generations.

SUMMARY OF THE INVENTION

Plants of the new *Lobularia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Inlobu1007'. These characteristics in combination distinguish 'Inlobu1007' as a new and distinct *Lobularia* plant:

1. Compact, outwardly spreading, mounding and semi-trailing plant habit.
2. Freely branching habit.
3. Freely and continuous flowering habit.
4. Relatively long flowering period.
5. Small violet-colored flowers.
6. Good garden performance.

Plants of the new *Lobularia* differ from plants of the female parent, 'Inlbusnopr', in the following characteristics:

1. Plants of the new *Lobularia* are more compact than and not as open as plants of 'Inlbusnopr'.
2. Plants of the new *Lobularia* have shorter internodes than plants of 'Inlbusnopr'.
3. Plants of the new *Lobularia* and 'Inlbusnopr' differ in flower color as flowers of plants of 'Inlbusnopr' are white in color.

Plants of the new *Lobularia* differ from plants of the male parent selection primarily in flower size as plants of the new *Lobularia* have smaller flowers than plants of the male parent selection.

Plants of the new *Lobularia* can be compared to (*Lobularia canariensis*×*Lobularia maritima*)×*Lobularia maritima* 'Inlbublupr', disclosed in U.S. Plant Pat. No. 24,516. In side-by-side comparisons, plants of the new *Lobularia* differed from plants of 'Inlbublupr' in the following characteristics:

1. Plants of the new *Lobularia* were not as vigorous as plants of 'Inlbublupr'.
2. Plants of the new *Lobularia* and 'Inlbublupr' differed in flower color as flowers of plants of 'Inlbublupr' were white in color.

Plants of the new *Lobularia* can be compared to (*Lobularia canariensis*×*Lobularia maritima*)×*Lobularia maritima* 'Inlbupripr', not patented. In side-by-side comparisons, plants of the new *Lobularia* differed from plants of 'Inlbupripr' in the following characteristics:

1. Plants of the new *Lobularia* were more vigorous than plants of 'Inlbupripr'.
2. Plants of the new *Lobularia* and 'Inlbupripr' differed in leaf color as plants of 'Inlbupripr' had green and yellow-variegated leaves.
3. Plants of the new *Lobularia* and 'Inlbupripr' differed in flower color as flowers of plants of 'Inlbupripr' were off-white in color.

BRIEF DESCRIPTION OF THE PHOTOGRAPHS

The accompanying colored photographs illustrate the overall appearance of the new *Lobularia* plant showing the colors as true as it is reasonably possible to obtain in colored reproductions of this type. Colors in the photographs may differ slightly from the color values cited in the detailed botanical description which accurately describe the colors of the new *Lobularia* plant.

The photograph at the bottom of the sheet comprises a side perspective view of a typical flowering plant of 'Inlobu1007' grown in a container.

The photograph at the top of the sheet is a close-up view of a typical flowering plant of 'Inlobu1007'.

DETAILED BOTANICAL DESCRIPTION

The aforementioned photographs and following observations, measurements and values describe plants grown during the spring in 10-cm containers in a polyethylene-covered greenhouse and subsequently in an outdoor nursery in Bonsall, Calif. During the production of the plants, day temperatures averaged 24° C. and night temperatures ranged from 13° C. to 16° C. Plants were pinched two times and were six weeks old when the photographs and description were taken. In the following description, color references are made to The Royal Horticultural Society Colour Chart, 2007 Edition, except where general terms of ordinary dictionary significance are used.

Botanical classification: (*Lobularia canariensis*×*Lobularia maritima*)×*Lobularia maritima* 'Inlobu1007'.

Parentage:

*Female, or seed, parent.*—*Lobularia canariensis*×*Lobularia maritima* 'Inlbusnopr', disclosed in U.S. Plant Pat. No. 21,594.

*Male, or pollen, parent.*—Unnamed selection of *Lobularia maritima*, not patented.

Propagation:

*Type.*—Terminal vegetative cuttings.

*Time to initiate roots, summer.*—About four to five days at temperatures of about 18° C. to 24° C.

*Time to initiate roots, winter.*—About five to seven days at temperatures of about 7° C. to 16° C.

*Time to produce a rooted young plant, summer.*—About four weeks at 18° C. to 24° C.

*Time to produce a rooted young plant, winter.*—About six weeks at 7° C. to 16° C.

*Root description.*—Medium in thickness, fibrous; white in color.

*Rooting habit.*—Moderately freely branching; medium density.

Plant description:

*Plant form and growth habit.*—Compact, outwardly spreading, mounding and semi-trailing plant habit; freely branching habit with about eight primary lateral branches each with numerous secondary lateral branches developing per plant; dense and bushy appearance; vigorous growth habit.

*Plant height.*—About 16 cm.

*Plant diameter* (*area of spread*).—About 36.5 cm.

*Lateral branches.*—Length: About 22 cm. Diameter: About 2.5 mm. Internode length: About 1.8 cm. Strength: Strong, flexible; with flower development, falling outwardly then curving upwardly. Texture: Pubescent; longitudinally ridged. Color: Close to 144A.

Leaf description:

*Arrangement.*—Alternate; simple.

*Length.*—About 3.4 cm.

*Width.*—About 9 mm.

*Shape.*—Narrowly obovate.

*Apex.*—Rounded to broadly acute.

*Base.*—Attenuate.

*Margin.*—Entire.

*Texture, upper and lower surfaces.*—Pubescent.

*Venation pattern.*—Single midvein.

*Color.*—Developing leaves, upper surface: Close to 137B. Developing leaves, lower surface: Close to 137C. Fully expanded leaves, upper and lower surfaces: Close to 137B; venation, close to 144A.

*Petioles.*—Length: About 6 mm. Diameter: About 1.5 mm. Texture, upper surface: Scattered pubescence. Texture, lower surface: Smooth. Color, upper and lower surfaces: Close to 144A.

Flower description:

*Flower type and habit.*—Small single rounded flowers arranged in narrow and loose terminal racemes; flowers face mostly outwardly; freely flowering habit, about 110 flowers potentially developing per inflorescence.

*Natural flowering season.*—Relatively long flowering period; plants flower continuously from early spring until late autumn in southern California.

*Flower longevity on the plant.*—About five to seven days; flowers not persistent.

*Fragrance.*—Faintly fragrant; sweet, vanilla-like.

*Inflorescence height.*—About 8.5 cm to 9 cm.

*Inflorescence diameter.*—About 3 cm.

*Flower diameter.*—About 5 mm.

*Flower depth* (*height*).—About 3 mm.

*Flower buds.*—Length: About 2 mm. Diameter: About 3 mm. Shape: Roughly spherical. Color: Close to N88C.

*Petals.*—Quantity and arrangement: Four petals arranged in a single whorl. Length: About 4 mm. Width: About 3.5 mm. Shape: Oval. Apex: Rounded. Base: Attenuate to oblique. Margin: Entire. Texture, upper and lower surfaces: Smooth, glabrous; velvety. Color: When opening, upper surface: Close to N82D. When opening, lower surface: Close to N82A to N82B. Fully opened, upper surface: Close to 86A; color becoming closer to 79B with development. Fully opened, lower surface: Close to 83B; color does not change with development.

*Sepals.*—Quantity and arrangement: Four sepals arranged in a single whorl; calyx, cup-shaped. Length: About 1.5 mm. Width: About 1 mm. Shape: Elliptical, short. Apex: Acute. Base: Truncate. Margin: Entire. Texture, upper surface: Smooth, glabrous.

Texture, lower surface: Pubescent; minute. Color, upper surface: Close to 148A. Color, lower surface: Close to N79A.

*Peduncles*.—Length: About 2.6 cm. Width: About 2 mm. Strength: Strong. Texture: Pubescent. Color: Close to 144B.

*Pedicels*.—Length: About 9 mm. Width: About 1 mm. Strength: Moderately strong. Texture: Scattered pubescence. Color: Close to 147B.

*Reproductive organs*.—Stamens: Quantity per flower: Six. Filament length: About 1.5 mm. Filament color: Close to 145D. Anther shape: Oval. Anther length: Less than 1 mm. Anther color: Close to 14A. Pollen amount: Scarce. Pollen color: Close to 14C. Pistils: Quantity per flower: One. Pistil length: About 2 mm. Style length: Less than 1 mm. Style color: Close to 137D tinted with close to 79B. Stigma shape: Rounded. Stigma color: Close to 145B. Ovary color: Close to 137D tinted with close to 79B.

*Seeds and fruits*.—Seed and fruit production have not been observed on plants of the new *Lobularia*.

Pathogen & pest resistance: Plants of the new *Lobularia* have not been noted to be resistant to pathogens or pests common to *Lobularia* plants.

Garden performance: Plants of the new *Lobularia* have been observed to have good garden performance and to tolerate temperatures ranging from about 4° C. to about 35° C.

It is claimed:

1. A new and distinct *Lobularia* plant named 'Inlobu1007' as illustrated and described.

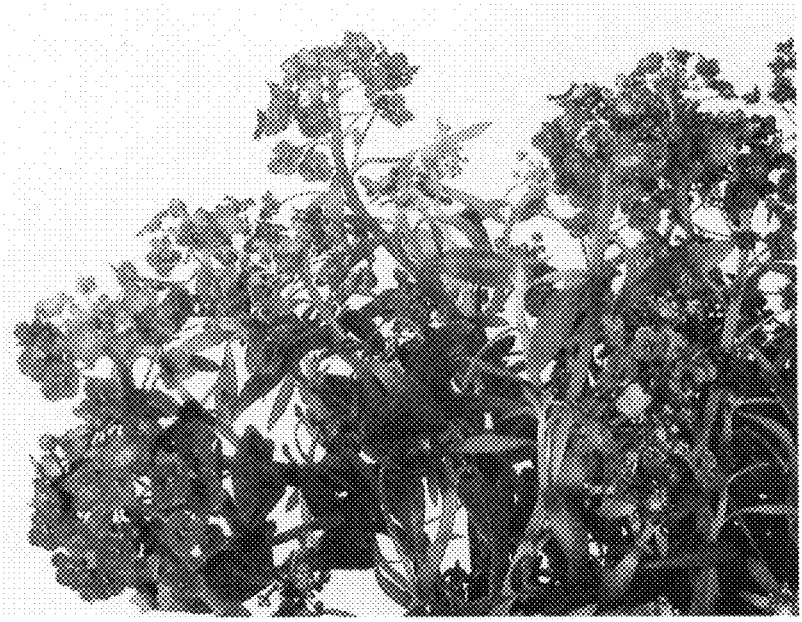
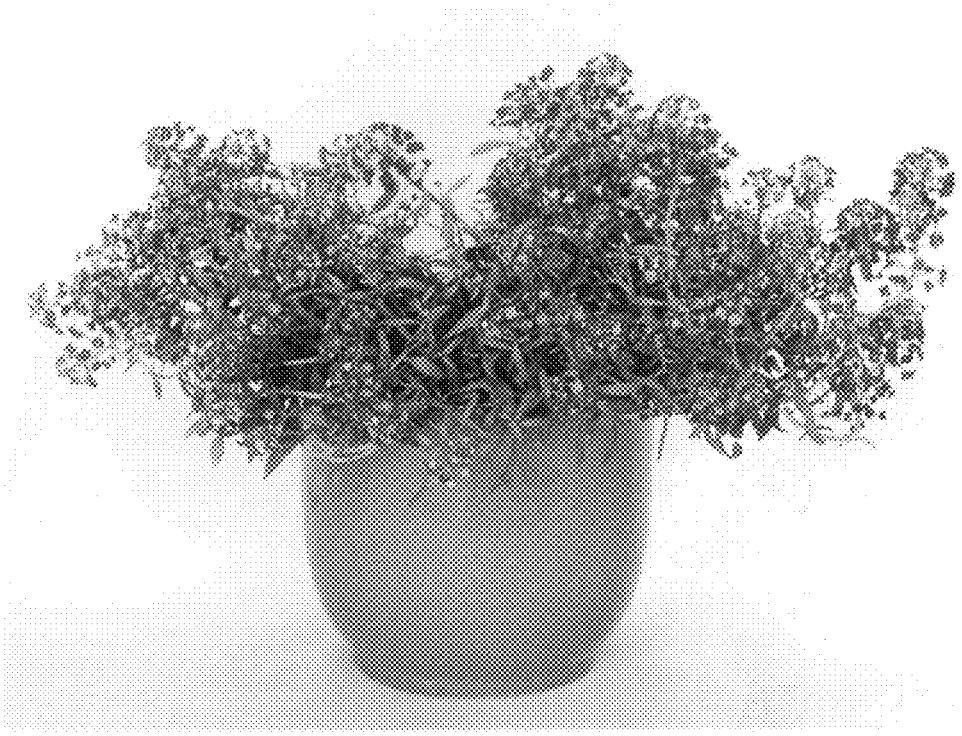

* * * * *